US010048196B2

United States Patent
Harb et al.

(10) Patent No.: US 10,048,196 B2
(45) Date of Patent: Aug. 14, 2018

(54) CAVITY ENHANCED SPECTROSCOPY USING OFF-AXIS PATHS

(71) Applicant: NewSouth Innovations Pty Limited, New South Wales (AU)

(72) Inventors: Charles Charbel Harb, Bungendore (AU); Toby Kristian Boyson, Royalla (AU)

(73) Assignee: NewSouth Innovations Pty Limited, New South Wales (AU)

( * ) Notice: Subject to any disclaimer, the term of this patent is extended or adjusted under 35 U.S.C. 154(b) by 0 days.

(21) Appl. No.: 15/336,045

(22) Filed: Oct. 27, 2016

(65) Prior Publication Data
US 2017/0067822 A1    Mar. 9, 2017

Related U.S. Application Data

(63) Continuation of application No. PCT/AU2015/000581, filed on Sep. 24, 2015.

(30) Foreign Application Priority Data

Oct. 3, 2014    (AU) ................................ 2014903960

(51) Int. Cl.
*G01N 21/00*     (2006.01)
*G01N 21/39*     (2006.01)
(Continued)

(52) U.S. Cl.
CPC ............ *G01N 21/39* (2013.01); *G01J 3/0208* (2013.01); *G01J 3/433* (2013.01); *G01N 21/031* (2013.01);
(Continued)

(58) Field of Classification Search
CPC ................. G01N 21/39; G01N 21/031; G01N 2021/391; G01N 2021/8411; G01J 3/433; G01J 3/0208; G01J 2003/4334
(Continued)

(56) References Cited

U.S. PATENT DOCUMENTS

| 5,912,740 A * | 6/1999 | Zare .......................... G01J 3/10 356/437 |
| 6,233,052 B1 * | 5/2001 | Zare ........................ G01N 21/39 250/343 |

(Continued)

FOREIGN PATENT DOCUMENTS

| WO | WO 2012/021943 | 2/2012 |
| WO | WO 2014/032078 | 3/2014 |
| WO | WO 2016/049679 | 4/2016 |

*Primary Examiner* — Tarifur Chowdhury
*Assistant Examiner* — Isiaka Akanbi
(74) *Attorney, Agent, or Firm* — Levine Bagade Han LLP (57) ABSTRACT

Methods and apparatuses of generating and processing a real-time time-domain cavity ringdown spectroscopy (CRDS) signal from absorbing species in an optical detection system having an optical ringdown cavity using off-axis paths are provided. At least one modulated light signal is generated using one or more light sources, each modulated at specified modulation frequency. Each modulated signal has harmonic frequency components and is input off-axis relative to the cavity's optical axis. The cavity contains mirrors arranged in a predetermined configuration. The optical axis is defined by a path passing through centers of mirrors. The modulated light signal is resonated off axis without astigmatic optical elements to produce CRDS signal and passes at least twice through cavity and across the mirrors without interfering with itself. An overall path length through cavity is greater than path length of optical axis. A photodetector detects the CRDS signal, which is demodulated dependent upon selected harmonics.

25 Claims, 4 Drawing Sheets

(51) Int. Cl.
  *G01N 21/03* (2006.01)
  *G01J 3/433* (2006.01)
  *G01J 3/02* (2006.01)
(52) U.S. Cl.
  CPC ............. *G01J 2003/4332* (2013.01); *G01J 2003/4334* (2013.01); *G01N 2021/391* (2013.01); *G01N 2201/0691* (2013.01)
(58) Field of Classification Search
  USPC .......................... 356/432, 437, 438, 480
  See application file for complete search history.

(56) References Cited

U.S. PATENT DOCUMENTS

| | | | |
|---|---|---|---|
| 6,795,190 B1 | 9/2004 | Paul et al. | |
| 7,468,797 B1 | 12/2008 | O'Keefe et al. | |
| 2002/0101592 A1* | 8/2002 | Zare | G01N 21/39 356/432 |
| 2006/0181710 A1* | 8/2006 | Kachanov | G01N 21/39 356/437 |
| 2010/0014094 A1* | 1/2010 | Cole | G01J 3/42 356/480 |
| 2013/0144561 A1 | 6/2013 | Harb et al. | |

* cited by examiner

CAVITY ENHANCED SPECTROSCOPY USING OFF-AXIS PATHS

CROSS-REFERENCE TO RELATED APPLICATIONS

This application is a continuation of PCT Patent Application Number PCT/AU2015/000581 filed on Sep. 24, 2015, which claims priority to Australian Patent Application 2014903960 filed Oct. 3, 2014, the contents of which are incorporated herein by reference in their entirety.

TECHNICAL FIELD

The present invention relates to methods and systems for generating and analysing cavity ringdown spectroscopy (CRDS) signals.

BACKGROUND

Any discussion of the background art throughout the specification should in no way be considered as an admission that such background art is prior art, nor that such background art is widely known or forms part of the common general knowledge in the field.

The detection of substances posing chemical, biological and explosives (CBE) threats has become critical in recent years, for example, for airport security.

U.S. Pat. No. 6,795,190 (U.S. Ser. No. 09/976,549) issued 21 Sep. 2004 in the name of Paul et al describes an absorption spectroscopy instrument with off-axis light insertion into a cavity. This instrument is described as allowing optical cavities to be used simply and effectively as absorption cells for the purpose of performing sensitive absorption spectroscopy. A continuous-wave light beam is introduced into the cavity using an off-axis cavity alignment geometry, which eliminates resonances commonly associated with optical cavities, while preserving the absorption signal amplifying properties of such cavities. Doing so is said to reduce the complexity of the instrument compared with other optical cavity-based absorption methods when applied in conjunction with integrated cavity output spectroscopy (ICOS).

Such off-axis cavity-enhanced spectroscopy is a variant of cavity ringdown spectroscopy (CRDS) that uses off axis paths (that is, the laser is coupled into the linear cavity at an angle away from the major axis) through a two-mirror resonator to measure the absorbance from a sample within the cavity. The result of such an off-axis path is that the cavity's mode structure collapses, and light is able to couple with a cavity mode more frequently. The absorbance is commonly measured with off-axis integrated cavity output spectroscopy (OA-ICOS): a detector is placed behind one of the cavity mirrors, and the intensity of the light exiting the cavity is measured as a function of wavelength. This OA-ICOS measurement is compared to one taken with no absorbing, sample in the cavity, along with a measurement of the ringdown time of the cavity (to determine the absolute loss due to the cavity mirrors), to generate an absorbance spectrum. This technique has advantages over traditional CRDS due to the simple experimental setup, and the fact the absolute alignment of the cavity relative to the laser beam is non-critical, which makes for a much more robust instrument. However, OA-ICOS technique has several disadvantages, including the measurement is taken at DC (i.e. there is no modulation on the light), so the effect of 1/f noise reduces the available sensitivity; the laser is coupled to the cavity during, a measurement, resulting in the laser's noise corrupting the measurement; and in order to achieve a dense mode structure, specialist astigmatic mirrors must be used.

The DC measurement used in OA-ICOS also does not allow the path length of the cavity to be measured (this is important for calculating an accurate absorption coefficient); such instruments need to measure the ringdown time throughout a measurement to calibrate the absorbance measurement from ICOS.

SUMMARY

The following definitions are provided as general definitions and should in no way limit the scope of the present invention to those terms alone, but are set forth for a better understanding of the following description.

Unless defined otherwise, all technical and scientific terms used herein have the same meaning as commonly understood by those of ordinary skill in the art to which the invention belongs. For the purposes of the present invention, the following terms are defined below:

The articles "a" and "an" are used herein to refer to one or to more than one (i.e. to at least one of the grammatical object of the article. By way of example, "an element" refers to one element or more than one element.

The term "about" is used herein to refer to quantities that vary by as much as 30%, preferably by as much as 20%, and more preferably by as much as 10% to a reference quantity.

Throughout this specification, unless the context requires otherwise, the words "comprise", "comprises" and "comprising" will be understood to imply the inclusion of a stated step or element or group of steps or elements, but not the exclusion of any other step or element or group of steps or elements.

The term "real time", for example "displaying real time data", refers to the display of the data without intentional delay, given the processing limitations of the system and the time required to accurately measure the data. Similarly, the phrase "analysing a signal in real time" refers to the analysis of a signal and presentation or output of data representative of the signal without intentional delay, given the processing limitations of the system and the time required to accurately analyse the signal and present the output of such analysis.

In accordance with an aspect of the invention, there is provided a method of generating and processing a real-time time-domain cavity ringdown spectroscopy (CRDS) signal from an absorbing species in an optical detection system having an optical ringdown cavity using off-axis paths. The optical ringdown cavity is adapted for accepting a sample of an absorbing species. The method comprises: generating at least one modulated light signal using one or more light sources, each light source being modulated at a specified modulation frequency, each modulated signal having, a plurality of harmonic frequency components; inputting the at least one modulated light signal off-axis to the optical ringdown cavity in relation to an optical axis of the optical ringdown cavity, the optical ringdown cavity comprising a plurality of mirrors arranged in a predetermined configuration within the optical ringdown cavity and the optical axis defined by a path passing through the centers of the mirrors, the mirrors being not astigmatic optical elements, different beamlines being established by the at least one modulated light signal and the mirrors interacting with the absorbing species sample; resonating off axis the at least one modulated light signal without astigmatic optical elements using the mirrors of the optical ringdown cavity to produce the CRDS signal, the modulated light signal passing at least two passes through the optical ringdown cavity and across the mirrors without interfering with itself, thereby increasing an overall path length through the optical ringdown cavity greater than the path length of the optical axis through the centers of the mirrors; and detecting using a photodetector the CRDS signal and demodulating the CRDS signal dependent upon selected harmonics of the modulated light signal.

A spot pattern may be produced across each mirror by the modulated light signal before interference with the modulated light signal itself occurs. An optimum spot pattern is produced having a maximum path length before interference occurs without using astigmatic optical elements in the optical ringdown cavity. The spot pattern may be cross- or square-shaped, or a Lissajous pattern. The Lissajous pattern maximises use of each mirror's surface and allows a long path length before the modulated light signal overlaps and interference occurs.

The optical ringdown cavity may comprise three mirrors arranged in a triangular configuration, or four mirrors arranged in a bowtie configuration. Other configurations and numbers of mirrors (e.g. 5 mirrors) may be practiced without departing from the scope of the invention.

The mode structure of the modulated light signal at the output of the optical ringdown cavity is stable.

At least two modulated light signals may be generated using light sources each having different wavelengths; each light source is modulated at a specified modulation frequency. The selectivity of the mirrors is dependent upon the modulation frequency of the modulated light signals and reflectivities of the mirrors. Further, each beamline is detected simultaneously using a single photodetector.

The at least one light source generating the at least one modulated light signal comprises a frequency comb. The method further comprises: dispersing wavelength components of the CRDS signal using an optical element, and measuring the dispersed wavelength components of the CRDS signal using, a photodetector array, the measured wavelength components of the CRDS signal being demodulated.

In accordance with another aspect of the invention, there is provided an apparatus for generating and processing a real-time time-domain cavity ringdown spectroscopy (CRDS) signal from an absorbing species in an optical detection system having an optical ringdown cavity using off-axis paths. The optical ringdown cavity is adapted for accepting a sample of an absorbing species. The apparatus comprises: one or more light sources generating at least one modulated light signal, each light source being modulated at a specified modulation frequency, each modulated signal having, a plurality of harmonic frequency components; a plurality of mirrors arranged in a predetermined configuration within the optical ringdown cavity; a mechanism for inputting the at least one modulated light signal off-axis to the optical ringdown cavity in relation to an optical axis of the optical ringdown cavity, the optical axis defined by a path passing through the centers of the mirrors, the mirrors being not astigmatic optical elements, different beamlines being established, by the at least one modulated light signal and the mirrors interacting with the absorbing species sample; the mirrors adapted for resonating off axis the at least one modulated light signal without astigmatic optical elements of the optical ringdown cavity to produce the CRDS signal, the modulated light signal passing at least two passes through the optical ringdown cavity and across the mirrors without interfering, with itself, thereby increasing an overall path length through the optical ringdown cavity greater than the path length of the optical axis through the centers of the mirrors; a photodetector for detecting the CRDS signal, and a demodulator demodulating, the CRDS signal dependent upon selected harmonics of the modulated light signal.

A spot pattern may be produced across each mirror by the modulated light signal before interference with the modulated light signal itself occurs. An optimum spot pattern is produced having a maximum path length before interference occurs without using astigmatic optical elements in the optical ringdown cavity. The spot pattern is cross- or square-shaped, or Lissajous pattern. The Lissajous pattern maximises use of each mirror's surface and allows a long path length before the modulated light signal overlaps and interference occurs.

The optical ringdown cavity may comprise three mirrors arranged in a triangular configuration, or four mirrors arranged in a bowtie configuration. Other configurations and numbers of mirrors (e.g. 5 mirrors) may be practiced without departing from the scope of the invention.

The mode structure of the modulated light signal at the output of the optical ringdown cavity is stable.

At least two modulated light signals may be generated using light sources each having different wavelengths; each light source is modulated at a specified modulation frequency. The selectivity of the mirrors is dependent upon the modulation frequency of the modulated light signals and reflectivities of the mirrors. Further, each hemline is detected simultaneously using a single photodetector.

The at least one light source generating the at least one modulated light signal comprises a frequency comb. The method further comprises: dispersing wavelength components of the CRDS signal using an optical element, and measuring the dispersed wavelength components of the CRDS signal using, a photodetector array, the measured wavelength components of the CRDS signal being demodulated.

The inputting mechanism may be implemented in any one of the following manners: at least one mirror disposed between the at least one light source and the optical ringdown cavity so that the at least one modulated light signal is input off-axis to the optical ringdown cavity in relation to an optical axis of the optical ringdown cavity; the at least one light source and the optical ringdown cavity are configured so that the at least one modulated light signal is input off-axis to the optical ringdown cavity in relation to an optical axis of the optical ringdown cavity; and the at least one light source being tilted relative to the optical ringdown cavity, or vice versa, so that the at least one modulated light signal is input off-axis to the optical ringdown cavity in relation to an optical axis of the optical ringdown cavity.

Various aspects of the optical detection systems may be implemented in accordance with the aspects of the methods described herein.

BRIEF DESCRIPTION OF DRAWINGS

Arrangements of the detection system are described hereinafter, by way of an example only, with reference to the accompanying drawings, in which.

DETAILED DESCRIPTION

Methods and optical detection systems for generating and processing a real-time time-domain cavity ringdown spectroscopy (CRDS) signal from an absorbing species in an optical detection system having an optical ringdown cavity are disclosed hereinafter. The optical ringdown cavity is adapted for accepting a sample of an absorbing species. In the following description, numerous specific details, including particular pulse rates, pulse durations, absorbing species, and the like are set forth. However, from this disclosure, it will be apparent to those skilled in the art that modifications and/or substitutions may be made without departing from the scope and spirit of the invention. In other circumstances, specific details may be omitted so as not to obscure the invention.

With reference to the drawings, systems and methods for digital detection for analysis of time-decaying signals are disclosed herein. By way of example, optical absorbance signals are detected and analysed.

Off-Axis CRDS Generally

The embodiments of the invention implement CRDS using off-axis paths and advantageous v provide a substantial improvement over the OA-ICOS technique, as follows:

(1) a multiple-mirror cavity is used to eliminate the need for astigmatic optics (i.e., OA-ICOS can be implemented without using astigmatic optics), and (2) the signal processing techniques disclosed in International (PCT) Patent Application Publication No. WO 2012/021943 published 23 Feb. 2012 in the names of NewSouth Innovations Pty Limited et al (PCT/AU2011/001071 filed 19 Aug. 2011), also published as U.S. Patent Application Publication No. 2013/0144561 A1 (U.S. Ser. No. 13/805,569) published 6 Jun. 2013 in the name of Harb et al., can be applied to reduce the influence of 1/f and laser noise.

The collapse of the mode structure of the optical ringdown cavity, which is essential for the technique, relies on the laser beam spot moving across the surface of the mirror, and not overlapping (cf. a standard CRDS measurement, where the beam is aligned on-axis in the cavity, and interferes with itself after a single round trip). The more round-trips the light makes in the cavity before interfering, the denser the mode structure, and the finer the spectral resolution of the measurement. This dense mode structure also eliminates the need for a system to stabilise the laser to the cavity. In addition, the now large number of modes increases the frequency of the laser's coupling to the cavity, increasing the duty cycle of the measurement. Using two spherical mirrors arranged as a Fabry-Perot cavity, and aligning off axis results in an ellipse of spots around the perimeter or area adjacent to the perimeter of the mirrors: the maximum number of round nips is limited by the physical size of the mirrors.

The use of a multiple-mirror cavity allows for a Lissajous spot pattern using standard optics. In addition, low reflectance input and output coupling mirrors can be used, simplifying the input and output of light to the cavity. Multiple-mirror cavities have non-degenerate polarisations, raising the possibility of having both a low and high finesse cavity at once. This potentially increases the dynamic range of the technique.

As noted hereinbefore, a traditional OA-ICOS measurement is taken at direct current (DC), resulting in 1/f noise limiting the sensitivity. In addition, a cavity ringdown measurement must be made after each scan to measure the loss due to the mirrors, which is non-ideal. Any time difference between the measurement and the baseline increases the effect of transient behaviour, and not measuring the mirror loss at all optical frequencies reduces the precision and accuracy, hi the embodiments of the invention, the signal processing technique disclosed in the noted International (PCT) Patent Application Publication No. WO 2012/021943 (also U.S. Patent Application Publication No. 2013/0144561 A1) is applied to remedy both of these problems. Such signal processing allows the measurement to be taken at a frequency higher than DC (typically, tens or hundreds of kHz), with a very narrow measurement bandwidth, which reduces the effects of both 1/f and laser noise.

The DC measurement used in OA-ICOS also does not allow the path length of the cavity to be measured (this is important for calculating an accurate absorption coefficient): In contrast to OA-ICOS instruments, the embodiments of the invention measure the ring down time directly throughout the whole measurement.

In addition to the use of a laser, the above is also relevant to frequency combs. Presently, cavity enhanced frequency comb experiments require complicated locking schemes to stabilise the frequency comb to the modes of the cavity. Using a multi mirror, off-axis cavity allows a frequency comb to pass through the cavity with no additional stabilisation. The data processing technique of International (PCT) Patent Application Publication No. WO 2012/021943 (also U.S. Patent Application Publication No. 2013/0144561 A1) can be applied if a wavelength dispersive element and detector array are used at the output of the cavity.

A laser or lasers may be aligned off-axis in terms of displacement and angle relative to the center of the input mirror of the cavity. This results in hundreds, perhaps thousands, of occurrences of a light beam bouncing around the mirrors before interference occurs.

The embodiments of the invention utilise off-axis paths in CRDS, without the ICOS technique. The embodiments of the invention can use more mirrors and do so in a number of configurations to implement longer paths before a beam interferes with itself, which is advantageous as the mode structure of the cavity is caused to collapse. Significantly, the additional mirrors allow a Lissajous path in the cavity. For example, three mirrors may be implemented in a triangle configuration, and four mirrors may be implemented in a bow-tie configuration.

Methods of generating and processing a real-time time-domain cavity ringdown spectroscopy (CRDS) signal from an absorbing species in an optical detection system are described hereinafter. The system has an optical ringdown cavity where off-axis paths are advantageously used in relation to mirrors configured in the cavity. The optical ringdown cavity is suitable for accepting a sample of an absorbing species. In this technique, one or more modulated light signals are generated using one or more light sources. Each light source is modulated at a specified modulation frequency. Each modulated signal has harmonic frequency components. Significantly, the modulated light signal(s) is input using a suitable mechanism to the optical ringdown cavity off-axis in relation to an optical axis of the optical ringdown cavity. The functionality of inputting the modulated light signal to the cavity may be implemented many different ways. For example, the modulated light signal may be input off-axis to the optical ringdown cavity in relation to the optical axis of the optical ringdown cavity using, any of the following mechanisms at least one mirror disposed between the light source and the optical ringdown cavity so that the modulated light signal is input off-axis; or the light source and the optical ringdown cavity are configured so that modulated light signal is input off-axis; or light source is tilted relative to the optical ringdown cavity, or vice versa, so that the modulated light signal is input off-axis.

In the optical ringdown cavity, a number of mirrors are arranged in a predetermined configuration within the optical ringdown cavity. The optical ringdown cavity may comprise three mirrors arranged in a triangular configuration, or four mirrors arranged in a bowtie configuration. Other configurations and numbers of mirrors (e.g. 5 mirrors) may be practiced without departing from the scope of the invention. Three is the minimum number of mirrors to be practiced in this system. The optical axis is defined b a path passing, through the centers of the mirrors. Significantly, the mirrors using in the cavity are not astigmatic optical elements. Different beamlines are established by: the modulated light signal, and the mirrors interacting with the absorbing species sample. The modulated light signal is resonated of axis, without astigmatic optical elements, using the mirrors of the optical ringdown cavity to produce the CRDS signal. The modulated light signal passes in at least two passes through the optical ringdown cavity and across the mirrors without interfering with itself, thereby increasing an overall path length through the optical ringdown cavity greater than the path length of the optical axis through the centers of the mirrors. A spot pattern may be produced across each mirror by the modulated light signal before interference with the modulated light signal itself occurs. An optimum spot pattern is produced having, a maximum path length before interference occurs without using astigmatic optical elements in the optical ringdown cavity. The spot pattern may be cross- or square-shaped, or a Lissajous pattern. The Lissajous pattern maximises use of each mirror's surface and allows a long path length before the modulated light signal overlaps and interference occurs.

A photodetector is used to detect the CRDS signal, which is demodulated dependent upon selected harmonics of the modulated light signal. The mode structure of the modulated light signal at the output of the optical ringdown cavity is stable.

In another arrangement, at least two modulated light signals input to the cavity off axis may be generated using light sources each having different wavelengths; each light source is modulated at a specified modulation frequency. The selectivity of the mirrors is dependent upon the modulation frequency of the modulated light signals and reflectivities of the mirrors. Further, each hemline may be detected simultaneously using a single photodetector.

Still further, at least one light source generating the at least one modulated light signal comprises a frequency comb. The method further comprises: dispersing wavelength components of the CRDS signal using an optical element, and measuring the dispersed wavelength components of the CRDS signal using a photodetector array, the measured wavelength components of the CRDS signal being demodulated.

Aspects of a CRDS system generally are described hereinafter, before continuing with a further description of the techniques in greater detail.

CRDS System Generally

Figure 1:
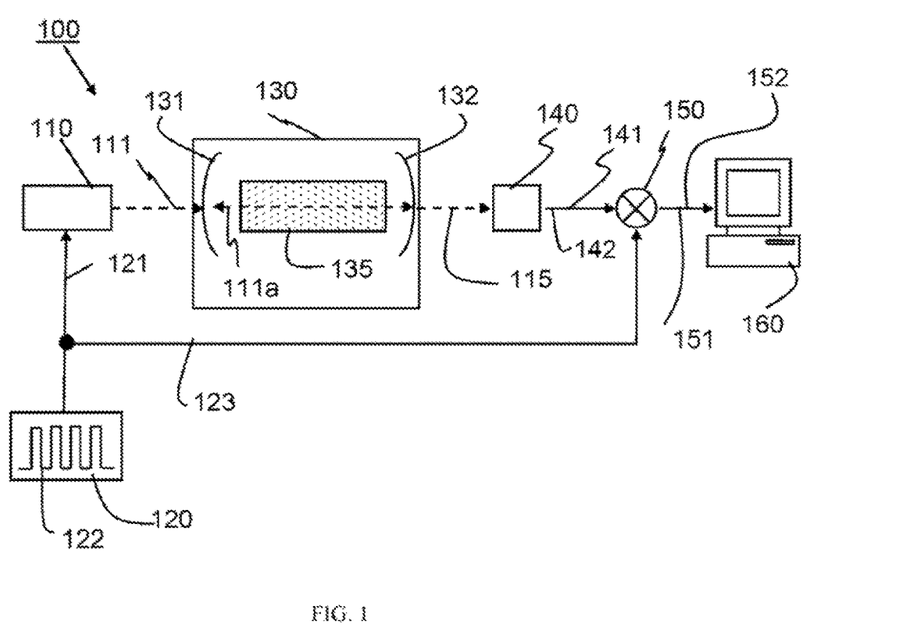
FIG. 1 is a block diagram illustrating a system for analysing a time-decay signal depicted in a CRDS application.

FIG. 1 depicts a simplified schematic of a system 100 for analysing a time-decay signal depicted in a CRDS application. This system is disclosed in detail in international (PCT) Patent Application Publication No. WO 2012/021943 (also, U.S. Patent Application Publication No. 2013/0144561 A1). Light source 110 (for example, one or more suitable laser sources), which may be a tunable laser source, is modulated. For example, this may be done using a square wave signal 122 from a modulator (local oscillator) 120 over communication line 121 to produce a quasi-continuous wave optical beam 111. For example, the light source 110 may be a quantum cascade laser. Other types of light sources and in particular lasers may be practiced. The beam 111 enters an optical cavity 130.

The optical ringdown cavity 130 is defined by reflectors 131 and 133, where each of the reflectors 131 and 133 has a reflectivity at the wavelength of the modulated optical beam 111 which is typical for CRDS systems, typically greater than 99.9%. The optical beam 111a resonates within the cavity 130. An absorbing sample 135 under analysis (for example, a gas-phase species) is located intermediate the reflectors 131 and 133, within the optical ringdown cavity 130 such that the optical beam 111 is at least partially absorbed in the optical ringdown cavity 130 by the sample 135. With each round trip of the cavity 130, a small portion of the optical beam 111a exits the cavity as a time-decay signal 115, and is detected by an optical detector or photodetector 140. Detector 140 may be, for example, a photomultiplier tube, photodiode or other suitable optical detector having a response time fast enough for detection of the time-decay signal.

The detected signal 141 is output from the detector 140 and input via a communication line 142 to a mixer module 150. Using the mixer module 150, the detected signal 141 is digitally mixed with a square wave having the same frequency as the ring-down waveform 115, which may be taken directly from the square wave modulation signal 122 output from the modulator 120 via a communication line 123. The mixer 150 may generate a transformed (demodulated) output signal 151, which is input via a communication line 152 to a determiner 160 (such as, for example, a computer or alternative determining device such as a calculator or similar device) adapted for analysing the transformed output signal 151. Presently described system 100 is an example of a digital demodulation system for analysing the cavity-ringdown time-decay (absorbance) signal 115 of the sample 135 situated in the optical ringdown cavity 130.

In practice, the light source 110 is typically a tunable laser source that is scanned over a frequency range of interest, and the absorbance is determined for frequencies within the scanned frequency range to generate an absorbance spectrum of the absorbing species (sample 135) over the scanned frequency range. Alternatively the light source may be a broadband light source, which outputs light in a range of frequencies, and the system may further comprise a scanning device (not shown) to scan across the range of output frequencies to thereby detect time-decay signals across the scanned frequencies to generate an absorbance spectrum of the absorbing species (sample 135) over the scanned frequency range.

The absorbance can be directly calculated from a measurement of the ringdown times with and without sample. The absorbance is calculated from the inverse of the difference between the background and sample ringdown times, as follows:

$$A(\lambda) = \frac{1}{c}\left(\frac{1}{\tau} - \frac{1}{\tau_0}\right) \qquad (1)$$

where A(lambda) is the absorbance at a given wavelength, c is the speed of light, tau_0 is the background ringdown time, and tan is the ringdown time with a sample in the optical ringdown cavity. Further, details of the determination of the absorbance of the species can be determined using the techniques disclosed in International (PCT) Patent Application Publication No. WO 2012/021943 (also, U.S. Patent Application Publication No. 2013/0144561 A1).

The embodiments of the invention described hereinafter may be practiced using the system 100 depicted in FIG. 1.

Off-Axis Paths in Optical Ringdown Cavity

Figure 2:
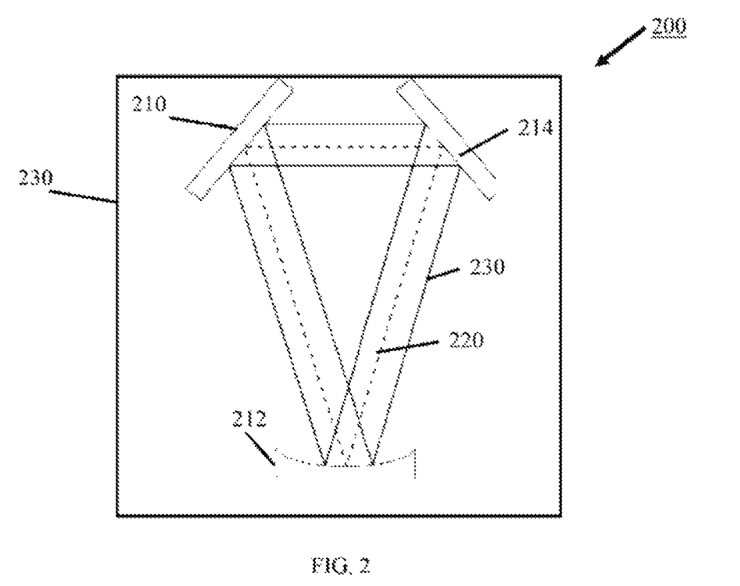
FIG. 2 is a block diagram illustrating on- and off-axis paths in a three mirror cavity, the on-axis path indicated with a dashed line and the off-axis path indicated with a solid line.

FIG. 2 shows an on- and off-axis path 500 in a three-mirror optical ringdown cavity 230, which may be practiced in the system 100 of FIG. 1 in place of the cavity 130. The inputs and outputs of the cavity 230 are not shown in FIG. 2 to simplify the drawing. The mirrors 210, 212, 214 are arranged in a triangular configuration. An on-axis path 220 is shown as a dashed line in FIG. 2. An off-axis path 230 is shown as a solid line. This is a two-dimensional (2-D) representation of the path, with only one out of a possible four (4) displacements applied, i.e. translational and angular displacement in the two dimensions orthogonal to the beam's travel direction. In an alternative arrangement, four mirrors could be configured in a bow-tie layout, for example.

Elliptical Spot Pattern from Off-Axis Path

Figure 3:
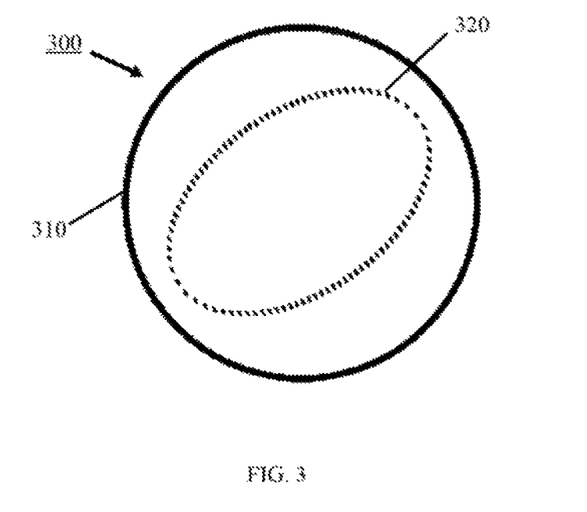
FIG. 3 is a diagram showing a beam path generated using a linear cavity without astigmatic optics, where the beam traces an ellipse on the surface of a cavity mirror.

FIG. 3 shows an arrangement 300 of a mirror 310 with a beam path 320 (dotted line) generated using a linear cavity with an off-axis path without astigmatic optics. The beam 320 traces an ellipse on the surfaces of mirrors 310 near or adjacent its perimeter. FIG. 3 shows a pattern that can be observed on an input cavity mirror 310. The spot pattern is present on all cavity mirrors. Each individual dot or spot represents a bounce of a light beam on the mirror 310. The aim of using the off-axis path is to maximise the number of bounces before the beam 320 returns to its original position.

Lissajous Spot Pattern from Off-Axis Path

Figure 4:
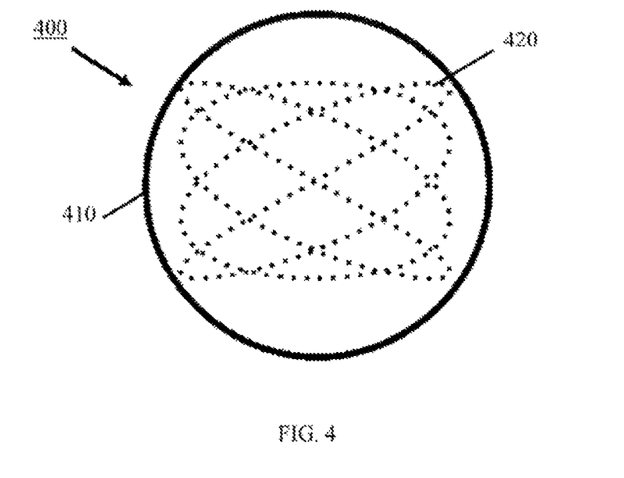
FIG. 4 is a diagram illustrating a beam path generated using as multiple-mirror optical ringdown cavity in accordance with an embodiment of the invention, which is like one generated using astigmatic optics, where the beam traces a Lissajous pattern on the mirrors' surfaces.

FIG. 4 shows an arrangement 400 of a mirror 410 with a beam path 420 (dotted line) generated using a multiple mirror cavity, producing a beam path like that generated using astigmatic optics and a linear cavity with an off-axis path. The beam 420 traces a Lissajous pattern on the surfaces of mirrors 410. FIG. 4 shows the expected pattern observed on an input cavity mirror 410. The spot pattern is present on all cavity mirrors. Again, each spot represents a bounce. The Lissajous pattern takes many more bounces (relative to the elliptical pattern) before the beam returns to its original position and is therefore a much more efficient use of the mirror surfaces.

Off-Axis CRDS Systems

Figure 5:
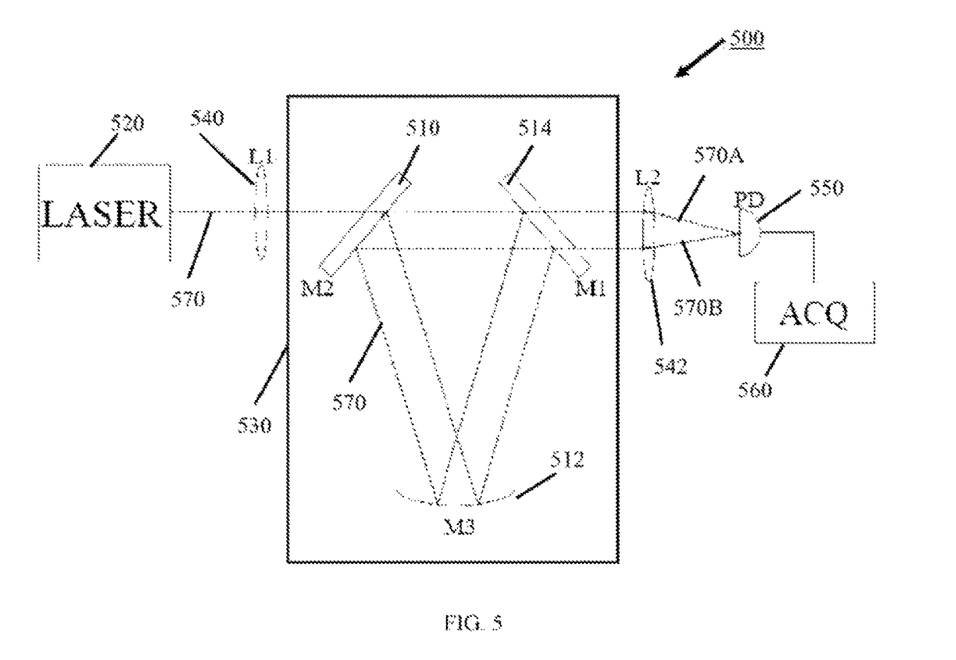
FIG. 5 is block diagram illustrating a system for generating and processing a real-time time-domain cavity ringdown spectroscopy (CRDS) signal from an absorbing species in accordance with an embodiment of the invention.

FIG. 5 shows a system 500 that may be practiced as part of the CRDS system of FIG. 1. This system 500 provides an apparatus that generates and processes a real-time time-domain CRDS signal from an absorbing species in an optical detection system having an optical ringdown cavity 530 using off-axis paths. The optical ringdown cavity 530 is adapted for accepting a sample of an absorbing species (not shown in FIG. 5). The light beam 570 output by a laser 520 is input off-axis into an optical ringdown cavity 830 containing three mirrors 510, 512, 514 in a triangular configuration, like that in FIG. 2, through a mode matching lens 540 (located between the laser 520 and the mirror 510. The light beam 570 output by the laser 520 is coupled into the cavity off axis. Practically, the light 570 can also be coupled off axis in an orthogonal dimension (coming out of the screen/page), and also angularly off axis in both dimensions. For the sake of simplifying the drawing, this is not depicted in FIG. 5.

FIG. 5 illustrates a single light source (laser) 520 generating a modulated light signal 570. While only a single light source 520 is shown, two or more light sources may be practiced. In this system 500, each light source 520 is modulated at a specified modulation frequency. The resulting modulated signal 570 has harmonic frequency components. Again, the optical axis of the optical ringdown cavity 530 is defined by a path passing through the centers of the mirrors 510, 512, 514. Any of a number of mechanisms may be practiced for inputting the modulated light signal 570 off-axis to the optical ringdown cavity 530 in relation to the optical axis (220 in FIG. 2). For example, this may be done in any of the following manners: one or more mirrors disposed between the light source 520 and the optical ringdown cavity 530; the light source 520 and the optical ringdown cavity 530 are configured so that the modulated light signal is input off-axis; and the light source 520 is tilted relative to the optical ringdown cavity, or vice versa.

Significantly, the mirrors 510, 512, 514 in this embodiment are not astigmatic optical elements. Different bean are established by the modulated light signal 570 and the mirrors 510, 512, 514 interacting with the absorbing species sample. The mirrors 510, 512, 514 of the optical ringdown cavity 530 are arranged in a predetermined configuration. In FIG. 5, the three mirrors 510, 512, 514 are arranged in a triangular configuration. Alternatively, four mirrors may be arranged in a bowtie configuration. Other configurations and numbers of mirrors (e.g. 5 mirrors) may be practiced without departing from the scope of the invention. The mirrors 510, 512, 514 are adapted for resonating off axis the modulated light signal 570, without astigmatic optical elements, of the optical ringdown cavity 530 to produce the CRDS signal 570A, 570B. The modulated light signal 570 passes at least two passes (only two passes are shown in FIG. 5) through the optical ringdown cavity 530 and across the mirrors 510, 512, 514 without interfering with itself. Consequently, the overall path length through the optical ringdown cavity 530 is greater than the path length of the optical axis through the centers of the mirrors 510, 512, 514.

In this system 500, a spot pattern, such as those 320 and 420 shown in FIGS. 3 and 4, can be produced across each mirror 310, 410, 510, 512, 514 by the modulated light signal 570 before interference with the modulated light signal 570 itself occurs. An optimum spot pattern is produced having a maximum path length before interference occurs without using astigmatic optical elements in the optical ringdown cavity 530. The spot pattern may be elliptical, cross- or square-shaped, or a Lissajous pattern. The Lissajous pattern maximises use of each mirror's surface and allows a long path length before the modulated light signal 570 overlaps and interference occurs.

The multiple beams 570A and 570B exit the cavity 530 (one per bounce on the mirror) and are focused using lens 542 onto a photodetector 550 for detecting the CRDS signal 570A, 570B. The optical paths 570 are shown as dashed lines, while the electrical connection between the photodetector 550 and the data acquisition system 560 is depicted with a solid line. The mode structure of the modulated light signal 570A, 570B at the output of the optical ringdown cavity 530 is stable. The system 500 shown in FIG. 5 may be embodied in the CRDS system shown in FIG. 1. The photodetector 550 may be photodiode based, an avalanche photodiode, or a photomultiplier tube. The output from the photodetector 550 goes to the acquisition module for data analysis. The data analysis is exactly the same as that shown in FIG. 1. Further information may be found at URL: http://www.opticsinfobase.org/oe/abstract.cfm?uri=oe-22-9-10519. A demodulator can demodulate the CRDS signal 570A, 570B dependent upon selected harmonics of the modulated light signal 570.

Again, the detected signal 141 is output from the detector 140 and input via a communication line 142 to a mixer module 150. Using the mixer module 150, the detected signal 141 is digitally mixed with a square wave having the same frequency as the ring-down waveform 115, which may be taken directly from the square wave modulation signal 122 output from the modulator 120 via a communication line 123. The mixer 150 may generate a transformed (demodulated) output signal 151, which is input via a communication line 152 to a determiner 160 (such as, for example, a computer or alternative determining device such as a calculator or similar device) adapted for analysing the transformed output signal 151. Presently described system 100 is an example of a digital demodulation system for analysing the cavity-ring-down time-decay (absorbance) signal 115 of the sample 135 situated in the optical ringdown cavity 130. Tau is calculated from the frequency components (i.e. the harmonics of the modulated signal) using the following expression:

$$\tau = \frac{1}{\omega}\sqrt{\left(\frac{1-P}{4P-1}\right)} \quad (2)$$

where omega is the angular modulation frequency (in rad/sec), and P is the ratio of the magnitudes of the first and second harmonic.

In another embodiment of the invention, at least two modulated light signals may be generated using light sources each having different wavelengths, with each light source being modulated at a specified modulation frequency. The selectivity of the mirrors is dependent upon the modulation frequency of the modulated light signals and reflectivities of the mirrors. Further, each beamline is detected simultaneously using a single photodetector.

Figure 6:
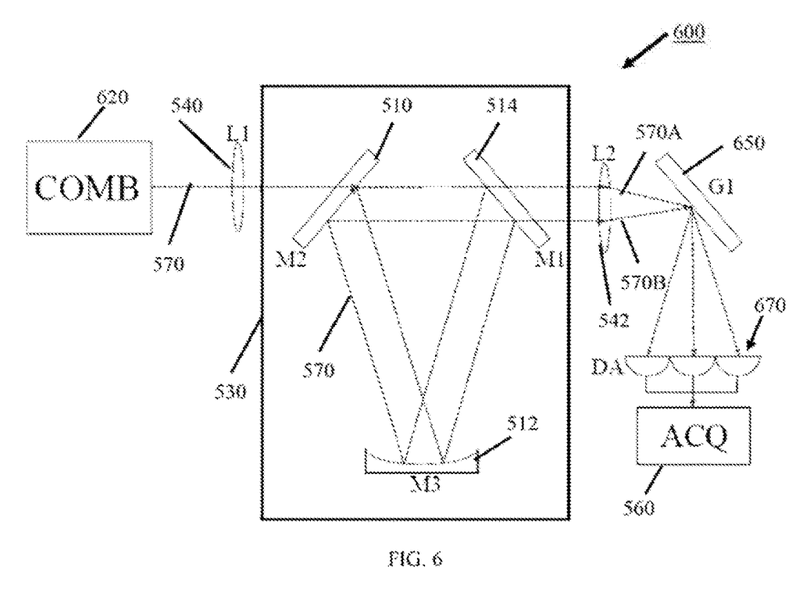
FIG. 6 is block diagram illustrating another system for generating and processing a real-time time-domain cavity ringdown spectroscopy (CRDS) signal from an absorbing species using a frequency comb in accordance with a further embodiment of the invention.

FIG. 6 illustrates another system 600 for generating and processing a real-time time-domain CRDS signal from an absorbing, species in an optical detection system having an optical ringdown cavity 530 using off-axis paths. This embodiment uses a frequency comb. For the sake of brevity only to avoid repetitious description, features of FIG. 5 that are the same in FIG. 6 use the same reference numerals (e.g., 530) and have the same functionality and configuration. Accordingly, the following description of FIG. 6 emphasizes those features that are different. The light source 520 of FIG. 5 is replaced in FIG. 6 with a frequency comb 620 (COMB). The output of the frequency comb 620 is input to the optical ringdown cavity 530, as per FIG. 5. Likewise, the CRDS signal 570A, 570B is output to an optical element 650 to disperse wavelength components of the CRDS signal 570A, 570B. This element may me a diffraction grating, a diffractive lens, or a prism. The dispersed wavelength components of the CRDS signal 570A, 570B are measured/detected using a photodetector array 670. The data acquisition system 560 acquires the detected signals. The measured wavelength components of the CRDS signal are demodulated.

In the embodiments of the invention, multiple-mirror cavities are used to avoid astigmatic optics. Further, the data processing technique of International (PCT) Patent Application Publication No. WO 2012/021943 (also, U.S. Patent Application Publication No. 2013/0144561 A1) is practiced.

Further Implementations

The method of International (PCT) Patent Application Publication No. WO 2014/032078 simultaneously demodulates using a single photodetector the CRDS signal dependent upon selected harmonics of the modulated light signals, which is important to the process of harmonic data extraction for a ring-down decay time constant.

The embodiments of the invention advantageously align the beam off axis. The beam must be off axis in at least one of the four dimensions of freedom.

Advantageously, the embodiments of the invention decreasing the cost of, and increase the throughput of, off-axis CRDS Thus, the systems and methods described herein and/or shown in the drawings are presented by way of example only and are not limiting as to the scope of the invention. Unless otherwise specifically stated, individual aspects and components of the signal generation and analysis methods and systems may be modified, or may have been substituted therefore known equivalents, or as yet unknown substitutes such as may be developed in the future or such as may be found to be acceptable substitutes in the future. The signal veneration and analysis methods and system may also be modified for a variety of applications while remaining within the scope and spirit of the claimed invention, since the range of potential applications is great, and since it is intended that the present signal generation and analysis methods and apparatus be adaptable to many such variations.

We claim:

1. A method of generating and processing a real-time time-domain cavity ringdown spectroscopy (CRDS) signal from an absorbing species in an optical detection system having an optical ringdown cavity using off-axis paths, said optical ringdown cavity adapted for accepting a sample of an absorbing species, said method comprising:

generating at least one modulated light signal using one or more light sources, each light source being modulated at a specified modulation frequency, each modulated signal having a plurality of harmonic frequency components;

inputting said at least one modulated light signal off-axis to said optical ringdown cavity in relation to an optical axis of said optical ringdown cavity, said optical ringdown cavity comprising a plurality of mirrors arranged in a predetermined configuration within said optical ringdown cavity and said optical axis defined by a path passing through the centers of said mirrors, said mirrors being not astigmatic optical elements, different beamlines being established by said at least one modulated light signal and said mirrors interacting with the absorbing species sample;

resonating off axis said at least one modulated light signal without astigmatic optical elements using said mirrors of the optical ringdown cavity to produce the CRDS signal, said modulated light signal passing at least two passes through the optical ringdown cavity and across said mirrors without interfering with itself, thereby increasing an overall path length through said optical ringdown cavity greater than the path length of the optical axis through the centers of said mirrors; and detecting using a photodetector the CRDS signal and demodulating the CRDS signal dependent upon selected harmonics of the modulated light signal.

2. The method as claimed in claim 1, wherein a spot pattern is produced across each mirror by the modulated light signal during the at least two passes.

3. The method as claimed in claim 2, wherein an optimum spot pattern is produced having a maximum path length before interference occurs without using astigmatic optical elements in said optical ringdown cavity.

4. The method as claimed in claim 2, wherein said spot pattern is cross- or square-shaped.

5. The method as claimed in claim 2, wherein said spot pattern is a Lissajous pattern.

6. The method as claimed in claim 5, wherein said Lissajous pattern maximises use of each mirror's surface and allows a long path length before the modulated light signal overlaps and interference occurs.

7. The method as claimed in claim 1, wherein said optical ringdown cavity comprises three mirrors arranged in a triangular configuration.

8. The method as claimed in claim 1, wherein said optical ringdown cavity comprises four mirrors arranged in a bowtie configuration.

9. The method as claimed in claim 1, wherein the mode structure of said modulated light signal at the output of said optical ringdown cavity is stable.

10. The method as claimed in claim 1, wherein:
at least two modulated light signals are generated using light sources each having different wavelengths, each light source being modulated at a specified modulation frequency;
the selectivity of said mirrors dependent upon said modulation frequency of said modulated light signals and reflectivities of said mirrors; and
each beamline is detected simultaneously using a single photodetector.

11. The method as claimed in claim 1, wherein the at least one light source generating said at least one modulated light signal comprises a frequency comb, and further comprising: dispersing wavelength components of the CRDS signal using an optical element, and measuring the dispersed wavelength components of the CRDS signal using a photodetector array, the measured wavelength components of the CRDS signal being demodulated.

12. The method as claimed in claim 1, exiting the CRDS signal from the optical ringdown cavity and focussing the CRDS signal using a focusing lens onto the photodetector.

13. An apparatus for generating and processing a real-time time-domain cavity ringdown spectroscopy (CRDS) signal from an absorbing species in an optical detection system having an optical ringdown cavity using off-axis paths, said optical ringdown cavity adapted for accepting a sample of an absorbing species, said apparatus comprising:
one or more light sources generating at least one modulated light signal, each light source being modulated at a specified modulation frequency, each modulated signal having a plurality of harmonic frequency components;
a plurality of mirrors arranged in a predetermined configuration within said optical ringdown cavity;

means for inputting said at least one modulated light signal off-axis to said optical ringdown cavity in relation to an optical axis of said optical ringdown cavity, said optical axis defined by a path passing through the centers of said mirrors, said mirrors being not astigmatic optical elements, different beamlines being established by said at least one modulated light signal and said mirrors interacting with the absorbing species sample;

said mirrors adapted for resonating off axis said at least one modulated light signal without astigmatic optical elements of the optical ringdown cavity to produce the CRDS signal, said modulated light signal passing at least two passes through the optical ringdown cavity and across said mirrors without interfering with itself, thereby increasing an overall path length through said optical ringdown cavity greater than the path length of the optical axis through the centers of said mirrors;

a photodetector for detecting the CRDS signal, and a demodulator demodulating the CRDS signal dependent upon selected harmonics of the modulated light signal.

14. The apparatus as claimed in claim 13, wherein a spot pattern is produced across each mirror by the modulated light signal during the at least two passes.

15. The apparatus as claimed in claim 14, wherein an optimum spot pattern is produced having a maximum path length before interference occurs without using astigmatic optical elements in said optical ringdown cavity.

16. The apparatus as claimed in claim 14, wherein said spot pattern is cross- or square-shaped.

17. The apparatus as claimed in claim 14, wherein said spot pattern is a Lissajous pattern.

18. The apparatus as claimed in claim 17, wherein said Lissajous pattern maximises use of each mirror's surface and allows a long path length before the modulated light signal overlaps and interference occurs.

19. The apparatus as claimed in claim 13, wherein said optical ringdown cavity comprises three mirrors arranged in a triangular configuration.

20. The apparatus as claimed in claim 13, wherein said optical ringdown cavity comprises four mirrors arranged in a bowtie configuration.

21. The apparatus as claimed in claim 13, wherein the mode structure of said modulated light signal at the output of said optical ringdown cavity is stable.

22. The apparatus as claimed in claim 13, wherein:
at least two modulated light signals are generated using light sources each having different wavelengths, each light source being modulated at a specified modulation frequency;
the selectivity of said mirrors dependent upon said modulation frequency of said modulated light signals and reflectivities of said mirrors; and
each beamline is detected simultaneously using a single photodetector.

23. The apparatus as claimed in claim 13, wherein the at least one light source generating said at least one modulated light signal comprises a frequency comb, and further comprising: an optical element for dispersing wavelength components of the CRDS signal, and a photodetector array for measuring the dispersed wavelength components of the CRDS signal, the measured wavelength components of the CRDS signal being demodulated.

24. The apparatus as claimed in claim 13, wherein said inputting means comprises:
at least one mirror disposed between said at least one light source and said optical ringdown cavity so that said at least one modulated light signal is input off-axis to said optical ringdown cavity in relation to an optical axis of said optical ringdown cavity; or said at least one light source and said optical ringdown cavity are configured so that said at least one modulated light signal is input off-axis to said optical ringdown cavity in relation to an optical axis of said optical ringdown cavity; or said at least one light source being tilted relative to the optical ringdown cavity, or vice versa, so that said at least one modulated light signal is input off-axis to said optical ringdown cavity in relation to an optical axis of said optical ringdown cavity.

25. The apparatus as claimed in claim 13 further comprising a focussing lens arranged to focus the CRDS signal onto the photodetector after the CRDS signal exits the optical ringdown cavity.

* * * * *